United States Patent [19]

Brennan

[11] Patent Number: 5,011,474
[45] Date of Patent: Apr. 30, 1991

[54] METHODS FOR CONTROLLING NASAL HEMORRHAGING

[76] Inventor: H. George Brennan, 1137 Granville, Newport Beach, Calif. 92660

[21] Appl. No.: 346,240

[22] Filed: May 2, 1989

Related U.S. Application Data

[63] Continuation-in-part of Ser. No. 197,835, May 24, 1988, Pat. No. 4,883,465.

[51] Int. Cl.$^5$ ............................................. A61M 31/00
[52] U.S. Cl. ........................................ 604/54; 604/94; 606/196
[58] Field of Search .................. 604/54, 73, 93, 94, 604/96–104, 285, 286, 358; 606/191, 192, 196, 199

[56] References Cited

U.S. PATENT DOCUMENTS

| | | |
|---|---|---|
| 6,796 | 10/1849 | Haile . |
| 923,303 | 6/1909 | Shults . |
| 1,051,850 | 1/1913 | Sandmark . |
| 1,114,268 | 10/1914 | Kells . |
| 1,235,095 | 7/1917 | Beck . |
| 1,766,341 | 6/1930 | Kulik . |
| 2,050,407 | 8/1936 | Wolff .................................. 128/246 |
| 2,179,964 | 11/1939 | Stevens . |
| 2,215,126 | 9/1940 | McMillin ........................... 128/148 |
| 2,265,387 | 12/1941 | McMillin ........................... 128/148 |
| 2,481,488 | 9/1949 | Auzin . |
| 2,485,184 | 10/1949 | Blackman et al. ..................... 604/94 |
| 2,490,168 | 12/1949 | Strauss ................................ 128/269 |
| 2,493,326 | 1/1950 | Trinder .............................. 128/325 |
| 2,647,515 | 8/1953 | Pollack et al. ..................... 128/325 |
| 2,677,375 | 5/1954 | Raiche .............................. 128/349 |
| 2,691,985 | 10/1954 | Newsom .............................. 128/342 |
| 2,847,997 | 8/1958 | Tibone .............................. 128/325 |
| 2,898,913 | 8/1959 | Ritter et al. ....................... 128/296 |
| 3,049,125 | 8/1962 | Kriwkowitsch ...................... 128/325 |
| 3,420,237 | 1/1969 | Fortay .............................. 128/325 |
| 3,502,078 | 3/1970 | Hill et al. ............................ 604/94 |
| 3,516,407 | 6/1970 | Ruggero ............................. 128/325 |
| 3,520,300 | 7/1970 | Flower, Jr. ......................... 128/276 |
| 3,547,126 | 12/1970 | Birtwell ............................. 128/349 |
| 3,570,494 | 3/1971 | Gottschalk ......................... 128/325 |
| 3,659,612 | 5/1972 | Shiley et al. ....................... 128/351 |
| 3,684,362 | 8/1972 | Holt ................................... 604/317 |
| 3,731,692 | 5/1973 | Goodyear ........................... 128/351 |
| 3,734,100 | 5/1973 | Walker et al. ..................... 128/351 |
| 3,753,439 | 8/1973 | Brugarolas et al. ................ 128/350 |
| 3,758,950 | 9/1973 | Krouzian .............................. 32/33 |
| 3,766,924 | 10/1973 | Pidgeon ............................. 128/325 |
| 3,850,176 | 11/1974 | Gottschalk ......................... 128/325 |

(List continued on next page.)

FOREIGN PATENT DOCUMENTS 2341833 2/1975 Fed. Rep. of Germany .
220978 6/1968 Sweden .

OTHER PUBLICATIONS

Arhelger, The Advantages of Tracheotomy and the use of a New Tracheal Tube, Surgery, Feb. 1951, p. 263.
Bernhard, et al., "Intracuff Pressures in Endotracheal and Tracheostomy Tubes", CHEST /87/6/Jun. 1985, pp. 720-725.
Robischon, Thomas, "Orange County, CA: A Hotbed of Medical-Technology Entrepreneurship", Medical Device and Diagnostic Industry, vol. 10, No. 1, Jan. 1988, pp. 36-39.

Primary Examiner—John D. Yasko
Assistant Examiner—Anthony Gutowski
Attorney, Agent, or Firm—Knobbe, Martens, Olson & Bear

[57] ABSTRACT

A method of controlling nasal hemorrhaging during a nasal procedure without exerting direct pressure on the area of bleeding utilizes a nasal tampon having an expansible sealing cuff. The tampon is inserted into the nasal cavity through the anterior nares until the expansible sealing cuff is disposed beyond the choanae. The expansible sealing cuff is then inflated, and the tampon slightly withdrawn into the nasal cavity so as to wedge the cuff between the choanae and the nasopharyngeal passageway and occlude the choanae. The tampon may also be adapted for connection to a source of suction so as to rapidly and continuously expel fluids from the nasal cavity.

6 Claims, 4 Drawing Sheets

U.S. PATENT DOCUMENTS

| | | | |
|---|---|---|---|
| 3,884,241 | 5/1975 | Walker | 128/325 |
| 3,884,242 | 5/1975 | Bazell et al. | 128/351 |
| 3,903,893 | 9/1975 | Scheer | 128/325 |
| 3,981,299 | 9/1976 | Murray | 128/349 |
| 4,030,504 | 6/1977 | Doyle | 128/325 |
| 4,102,342 | 7/1978 | Akyama et al. | 606/196 |
| 4,158,916 | 6/1979 | Adler | 32/33 |
| 4,182,385 | 1/1980 | Williamson | 141/65 |
| 4,233,025 | 11/1980 | Larson et al. | 433/136 |
| 4,243,033 | 1/1981 | Barrett | 128/215 |
| 4,315,505 | 2/1982 | Crandall et al. | 128/200.26 |
| 4,338,941 | 7/1982 | Payton | 128/325 |
| 4,403,611 | 9/1983 | Babbitt et al. | 604/94 |
| 4,488,548 | 12/1984 | Agdanowski | 128/204.25 |
| 4,508,533 | 4/1985 | Abramson | 604/35 |
| 4,568,326 | 2/1986 | Rangaswamy | 604/1 |
| 4,584,998 | 4/1986 | McGrail | 128/604 |
| 4,606,346 | 8/1986 | Berg et al. | 128/342 |

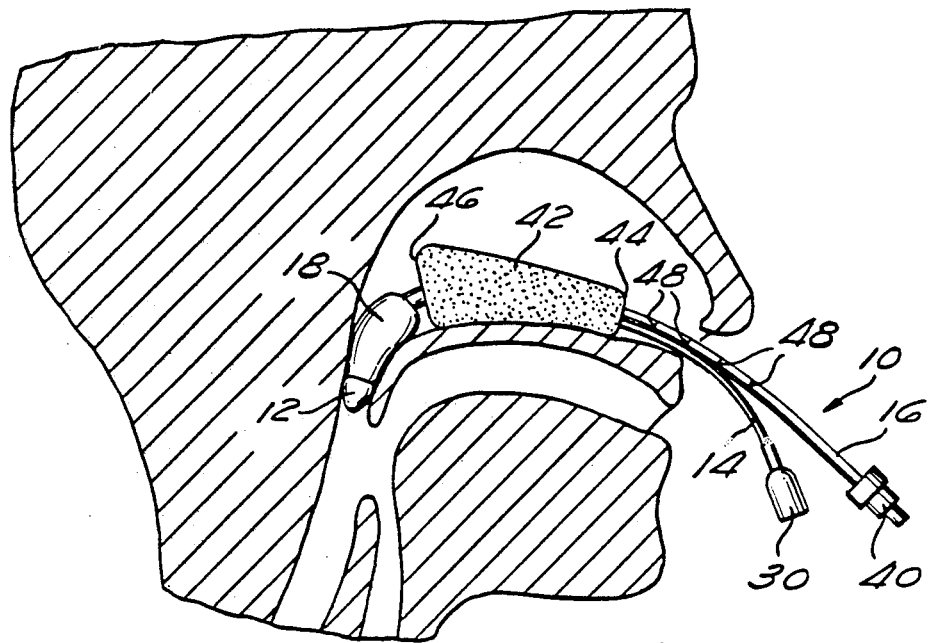
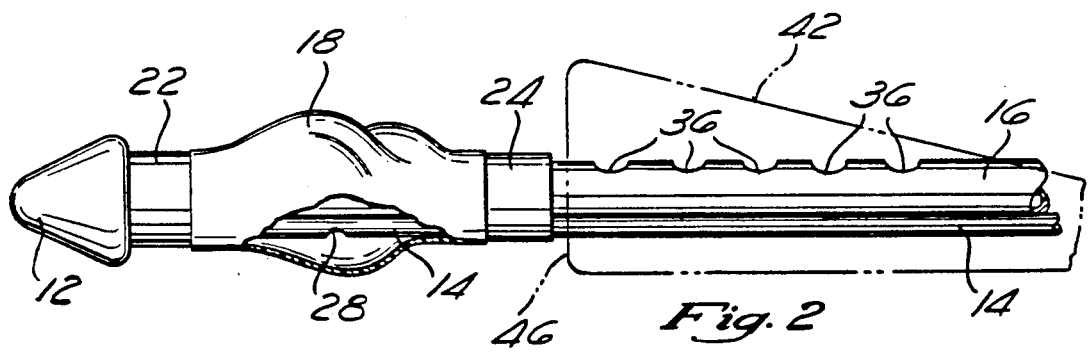
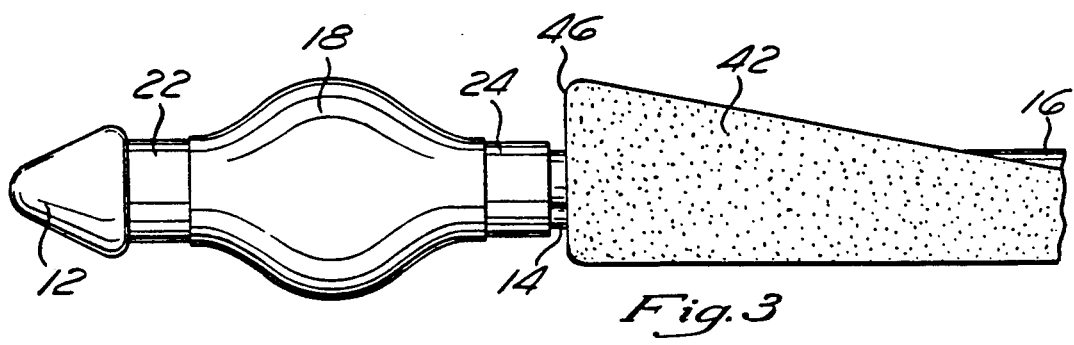

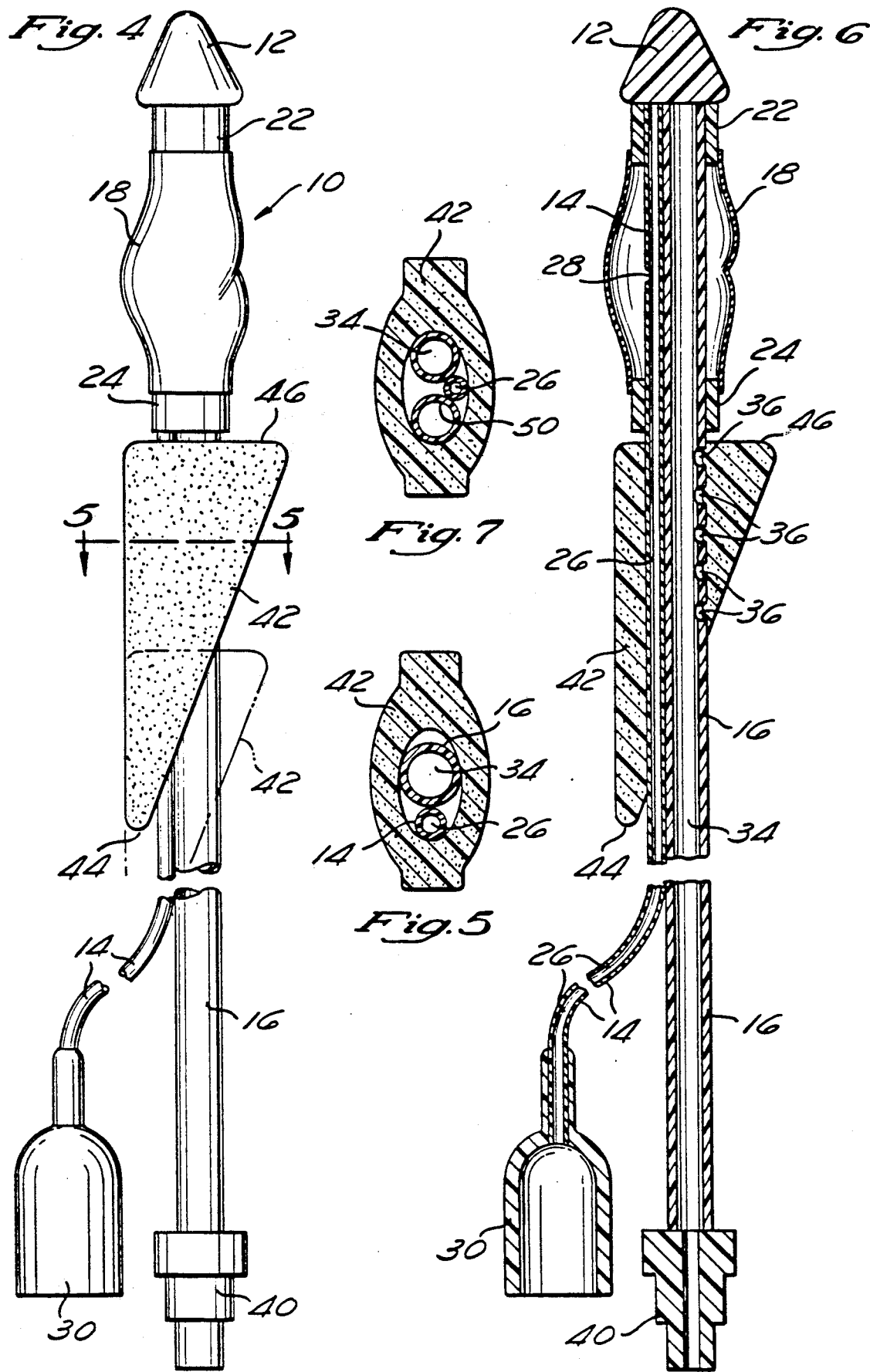

METHODS FOR CONTROLLING NASAL HEMORRHAGING

CROSS-REFERENCE TO RELATED APPLICATION

This application is a Continuation-In-Part of copending U.S. patent application Ser. No. 197,835, filed on May 24, 1988, which is now U.S. Pat. No. 4,883,465, enititled "NASAL TAMPON AND METHOD FOR USING".

BACKGROUND OF THE INVENTION

This invention relates to nasal tampons and, in particular, to an improved nasal tampon which is designed to occlude the choanae and at the same time permit aspiration of blood and other fluids seeping from an incision or wound. Although the apparatus of the present invention may be adapted to any of a variety of applications, it is particularly useful during and/or following rhinoplasty or other reconstructive or corrective surgical procedures in the vicinity of the nose.

Traditionally, nasal tampons have been used to arrest nasal hemorrhaging by exerting pressure on the area of bleeding. The general practice has been to pack the nasal cavity with absorbent material such as cotton, gauze and the like until a clot is formed and healing commenced. Use of such tampons typically causes a considerable amount of discomfort to the patient and can additionally damage the nasopharyngeal passageway due to pressure necrosis.

In the case of posterior nasal packing, a gauze or sponge plug secured to a catheter may be inserted through the anterior nares into the nasal cavity. The catheter is guided through the posterior choanae into the oral cavity and an end of the catheter is pulled out through the mouth, so as to draw the gauze or sponge plug up against the posterior choanae. As the sponge or gauze-like material fills with blood and other liquids, it swells and begins to occlude the choanae. However, as the sponge continues to absorb the fluids seeping from the incision or wound, the absorptivity decreases, and eventually, fluids escape the sponge and trickle down the patient's throat. When this occurs, the tampon must be removed, and a fresh tampon inserted. Since the sponge or gauze-like material of the tampon has a tendency to adhere to scabs and/or scar tissue within the nasal cavity, removal of the tampon can and often does result in additional bleeding. Further, while the tampon is being replaced, blood and other fluids are allowed to flow freely from the wound or incision and into the trachea, and down into the stomach which creates coughing, nausea and vomiting.

In an attempt to overcome the problems encountered with these gauze-like types of nasal tampons, catheter-like devices, having inflatable cuffs have been employed in the prior art. These catheters are inserted through the anterior nares in a deflated state, and after being properly positioned within the nasal cavity, the cuff is inflated to exert pressure on the bleeding area, and thereby arrest hemorrhaging. The inflatable cuffs used in the prior art nasal devices typically require use of sufficiently high pressure that may severely injure the tender mucosal membrane by prolonged contact therewith.

Further, if the nasal tampon is to be used during a surgical procedure to control hemorrhaging, it is imperative that sufficient working room is left for the surgeon. Nasal tampons which control bleeding by direct pressure are inappropriate for such surgical procedures, as the area to be operated upon is obstructed by the very nature of these types of tampons.

Aspirating devices are also commonly used to expel blood, mucous and other debris, occasioned by a surgical procedure. Such devices, however, frequently fail to prevent a portion of the fluids from entering the patient's throat. Moreover, direct contact between the intake of an aspirating device and the soft surrounding tissue can cause damage to the nasal mucosa and can contribute greatly to patient discomfort.

SUMMARY OF THE INVENTION

The present invention provides a novel nasal tampon which is readily adaptable to a variety of patient anatomies, and which eliminates many of the problems of prior art nasal tampons.

The present invention also provides a nasal tampon capable of suctioning out blood, mucous and other fluids present in the nasal cavity of a patient, due to a wound or incision without risk of direct suctioning of the soft surrounding tissue.

A significant feature of the preferred embodiment of the present invention is that it provides a nasal tampon having an expansible low pressure sealing cuff, constructed such that, when in the inflated condition, it presents an extended, low pressure cylindrical sealing surface for contacting the inner walls of the nasopharyngeal passageway with only a light pressure, while very effectively occluding the choanae to substantially eliminate the flow of blood and other liquids down the throat of a patient. This is highly advantageous in that when a patient swallows blood and it begins to accumulate in the stomach, the patient will become nauseous. The nausea induces vomiting, and causes the patient to strain, which raises the patient's venous and arterial pressure and ultimately induces an increase in bleeding.

Another significant advantage of the invention is that it controls hemorrhaging without direct pressure to the wound and leaves at least the frontal one-third of the nasal cavity clear for the performance of the surgical procedure.

Yet another significant feature of the present invention is the provision of a bypass breathing lumen. The breathing lumen allows the patient to breathe more naturally, through the nose, while the device is operatively installed.

These, as well as other features of the invention will become apparent from the detailed description of preferred embodiments which follows, considered together with the appended drawings.

BRIEF DESCRIPTION OF THE DRAWINGS

FIG. 1 is a diagrammatical elevational view of a human head illustrating a nasal cavity and a preferred embodiment of the improved nasal tampon of the present invention, operatively installed within the nasal cavity;

FIG. 2 is a perspective view of a preferred embodiment of the present invention, showing an absorptive sponge in phantom lines and a partial cut away view of the expansible cuff, in a deflated state;

FIG. 3 is a perspective view of the intranasal portion of the improved nasal tampon of the present invention, showing the expansible cuff in an inflated state;

FIG. 4 is a perspective view of the improved nasal tampon of the present invention, showing, in phantom lines, the ability of the sponge to move laterally along the inflation and drainage conduits;

FIG. 5 is a cross-sectional view, taken along line 5—5 of FIG. 4, showing the sponge and lumen arrangement;

FIG. 6 is a cross-sectional view, taken along line 6—6 of FIG. 4;

FIG. 7 is a cross-sectional view, similar to FIG. 5, but of an alternative embodiment, showing a third lumen which provides a breathing passageway, which enables the patient to breathe through the nose while the device is operatively installed;

DETAILED DESCRIPTION OF THE PREFERRED EMBODIMENT OF THE NASAL TAMPON

Figure 8:
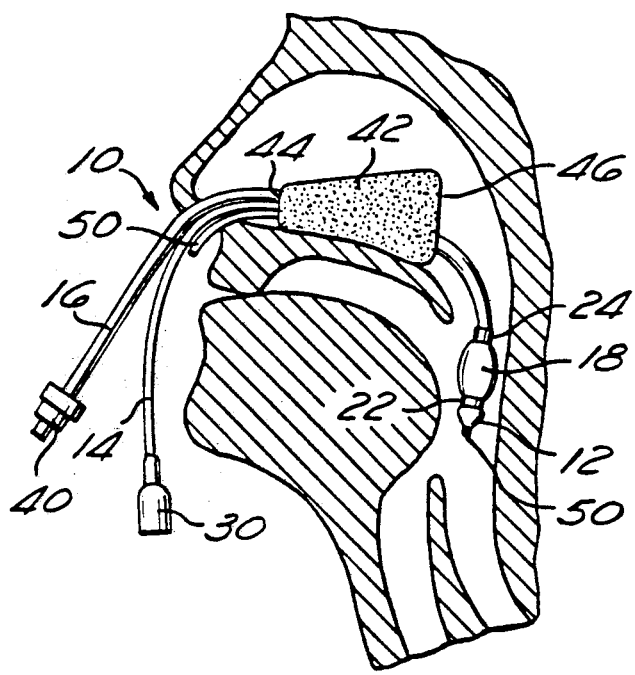
FIG. 8 is a diagrammatical elevational view of a human head illustrating a nasal cavity, having inserted therein an inflatable device for controlling a nasal hemorrhage.

Referring now to the drawings in detail, wherein like reference numerals designate like elements throughout the several views thereof, there is shown generally at 10, a nasal tampon, embodying the present invention in a preferred form, positioned in a nasal cavity in an inflated condition. The tampon 10 is a flexible device of sufficiently small diameter, which enables the tampon, in its deflated state, to be threaded through the anterior nares of a patient in catheter-like fashion. As shown in FIGS. 1, 4 and 6, the tampon 10 is tubular in shape, and comprises a blunt, tapered guiding end, having an inflation conduit 14 and a drainage conduit 16 contiguous therewith.

An expansible low pressure sealing cuff 18 surrounds the distal ends of the inflation and drainage conduits. The cuff 18 is constructed so that in the inflated condition it presents an extended cylindrical sealing surface for contacting the inner walls of the nasopharyngeal passageway. The cuff is dimensioned s that in its inflated state, it conforms to the interior walls of the choanae to occlude the passageway, yet does not interfere with the patient's swallowing or respiration through the mouth. By utilizing a cylindrically shaped surface, a low pressure seal may be formed with the choanae without applying excessive air pressure, since the seal extends over an extended axial length of the choanae. This extended surface allows an adequate seal to be formed so that only a low intracuff pressure of under 25 mmHg is applied to the soft mucosal tissue and therefore substantially eliminates the risk of damage due to pressure necrosis.

The guiding end 12 of the tampon 10 is preferably rounded and tapered, with no sharp edges to prevent damage to the mucous membrane, nerves and/or blood vessels when the device 10 is installed within the nasal cavity, and also to allow a fairly smooth surface continuation of the expansible low pressure sealing cuff 18. The expansible sealing cuff 18 is closed at opposite ends by a sealing attachment of its open ends to traverse walls 22, 24 respectively.

Extending longitudinally through the expansible low pressure sealing cuff 18 is a continuous, flexible hollow inflation conduit 14. The inflation conduit 14 has a small diameter, axially extending tubular passageway 26, having an opening 28 within the cavity of the expansible low pressure sealing cuff 18. The tubular passageway 26 is adapted to permit air or other pneumatic fluid to be transmitted through the tube and into the chamber enclosed by expansible low pressure sealing cuff 18 for inflation and deflation thereof.

To facilitate inflation of the expansible low pressure sealing cuff 18, a simple fluid valve 30 may be attached at the distal end of the conduit 14. This valve 30 is thus integrally connected to the inflation conduit 14 and may be easily manipulated to allow quick sealing of the pneumatic inflation conduit 14. The expansible low pressure sealing cuff 18 may be pressurized by inserting a hypodermic syringe (not shown) into the end of the inflation conduit 14 or, more preferably, into an enlarged opening (not shown) in the valve 30, with the valve in its open condition. By forcing air into the inflation conduit 14 with the hypodermic syringe, the expansible low pressure sealing cuff 18 may be inflated. It has been determined that approximately only 5 to 10 cc's of air will be sufficient to inflate the cuff 18 to a level which will provide an adequate seal with the choanae and thereby occlude the passageway. The valve 30 may then be closed and the hypodermic syringe removed, leaving the expansible low pressure sealing cuff 18 in an inflated state.

Adjacent to the inflation conduit 14 is a continuous, flexible hollow drainage conduit 16. As shown in FIG. 2, the drainage conduit 16, in relation to the inflation conduit 14, has a somewhat enlarged diameter, axially extending tubular passageway 34, having a plurality of influent ports 36, adjacent to the distal end thereof. Disposed at the proximal end of the drainage conduit 16, and integrally connected thereto, is a coupling device 40. The coupling device 40 provides a means by which the drainage conduit 16 may be connected to a source of suction (not shown), so as to expel blood and other debris, accumulated in front of the sealing cuff 18 from the nose of the patient. Well adapted to this purpose are leur type couplers, commonly used in connection with medical devices, friction fit couplers, or any conventional coupler which can be adapted to be connected to a source of suction. When using such suction types of devices, it is important that surrounding tissue is not inadvertently aspirated with the rest of the blood and other fluids which are desired to be expelled. Such aspiration of the tissue not only hampers the function of the device, but also causes great discomfort to the patient. To ensure that the soft tissue in the immediate vicinity of the influent ports 36 of the drainage conduit 16 are not suctioned into the device, a porous absorptive member 42 is provided. The absorptive member 42 is slidably mounted around the inflation and drainage conduits 14, 16, respectively, and serves to cover the influent ports 36 of the drainage conduit 16. In addition to preventing tissue from being suctioned into the influent ports 36 of the drainage conduit 16, the absorptive member 42 also acts to evenly distribute the vacuum across its entire surface.

Preferably, the absorptive member 42 is in the form of a surgical sponge. By way of example, a MEROCEL type sponge, as commercially available from and manufactured by AMERICAN CORPORATION, Mystic, Calif. may be employed. As depicted in the drawings, the absorptive member 42 advantageously has a tapered configuration such that the proximal end 44 has a smaller cross-sectional area than the distal end 46 thereof. This arrangement allows maximum absorptivity, while leaving sufficient working room for the surgeon to perform the surgical procedure. Preferably, the absorptive member 42 is sized so as to maintain at least the frontal one-third of the nasal cavity substantially clear. Further, as shown in FIG. 4, because the absorptive member 42 is slidably mounted around the inflation and drainage conduits, it may be slid laterally along the inflation and drainage conduits so as to provide additional working room, as required.

A material which is well adapted to construction of the present nasal tampon 10 is Poly Vinyl Chloride (PVC), such as Firestone's EXON No. 654 or Borden's VC-2605, made flexible with approximately 50% of a plasticizer, such as dioctyl phthalate. The conduits 14, 16 may be formed by injection molding from compounds such as Maclin's VM 2800 and VM 0400. Any conventional inert plasticizer such as adipate plasticizers or other phthalate esters can be used. The expansible low pressure sealing cuff 18 is formed with a higher quality of plasticizer to provide a greater flexibility.

The inflation conduit 14, drainage conduit 16, and expansible low pressure sealing cuff 18 are preferably constructed out of the same non-toxic polymer material. Dielectric heating of the polyvinyl chloride may be used to bind the ends 22, 24 of the cuff 18 to the inflation and drainage conduits 14, 16, respectively. The heating fuses the surfaces of these members into one another, and thus forms an integral pneumatic sealing bond. Alternatively, a plastisol may be used as a bonding agent to fix the ends of the sealing cuff 18 to the inflation and drainage conduits. By heat curing the plastisol, an air tight bond may be formed.

ALTERNATIVE EMBODIMENTS OF THE NASAL TAMPON

Due to the nature of the expansible low pressure sealing cuff 18, the nasal tampon 10 of the present invention can be operatively installed for any length of time: from a matter of minutes to a matter of days, without causing necrosis to the tissue with which it comes in contact. When the device is to be left in the nasal cavity for a prolonged period of time, it is preferable that breathing through the nose be permitted.

Figure 9:
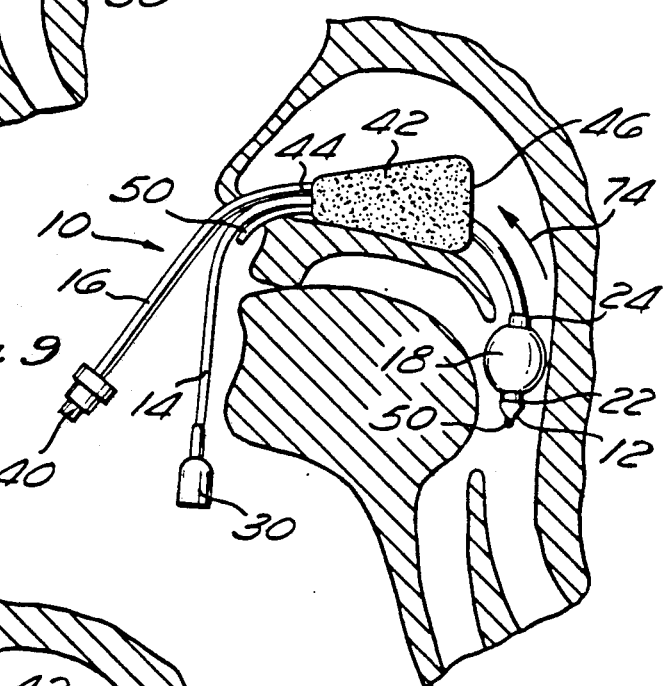
FIG. 9 is a diagrammatical view of the human head as illustrated in FIG. 8, illustrating the inflation of the inflatable device within the nasopharyngeal passageway and an arrowhead indicating that the device is to be slightly withdrawn through the anterior hares.
Figure 10:
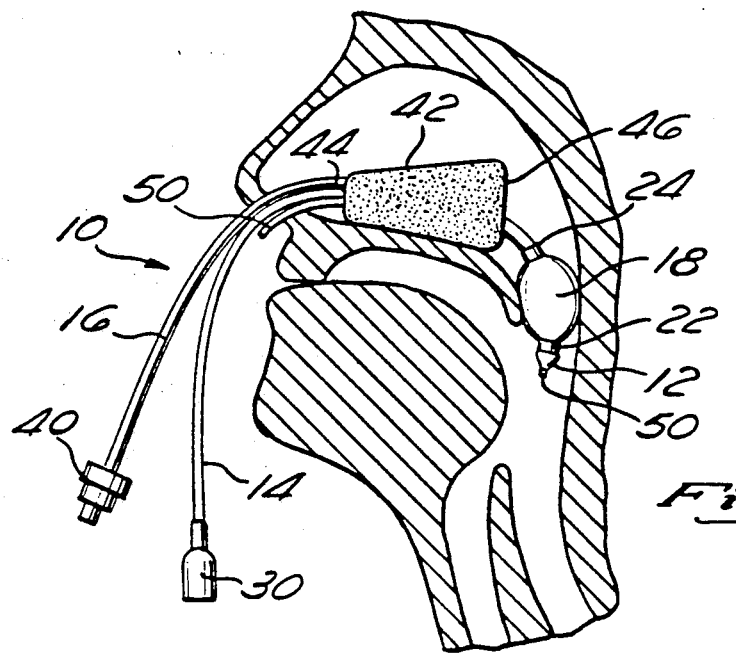
FIG. 10 is a diagrammatical view of the human head illustrating the occlusion of the nasopharyngeal passageway by the inflated device.

To this end, in an alternate embodiment, a third conduit 50, as shown in FIG. 8-10 and also in cross-section in FIG. 7, is provided. This breathing conduit 50 extends longitudinally through the expansible low pressure sealing cuff 18 and out the guiding end 12 of the tampon 10, bypassing the seal formed between the cuff 18 and the choanae. Thus, the patient is allowed to breathe through the nasal cavity in which the device is operatively installed.

Figure 11:
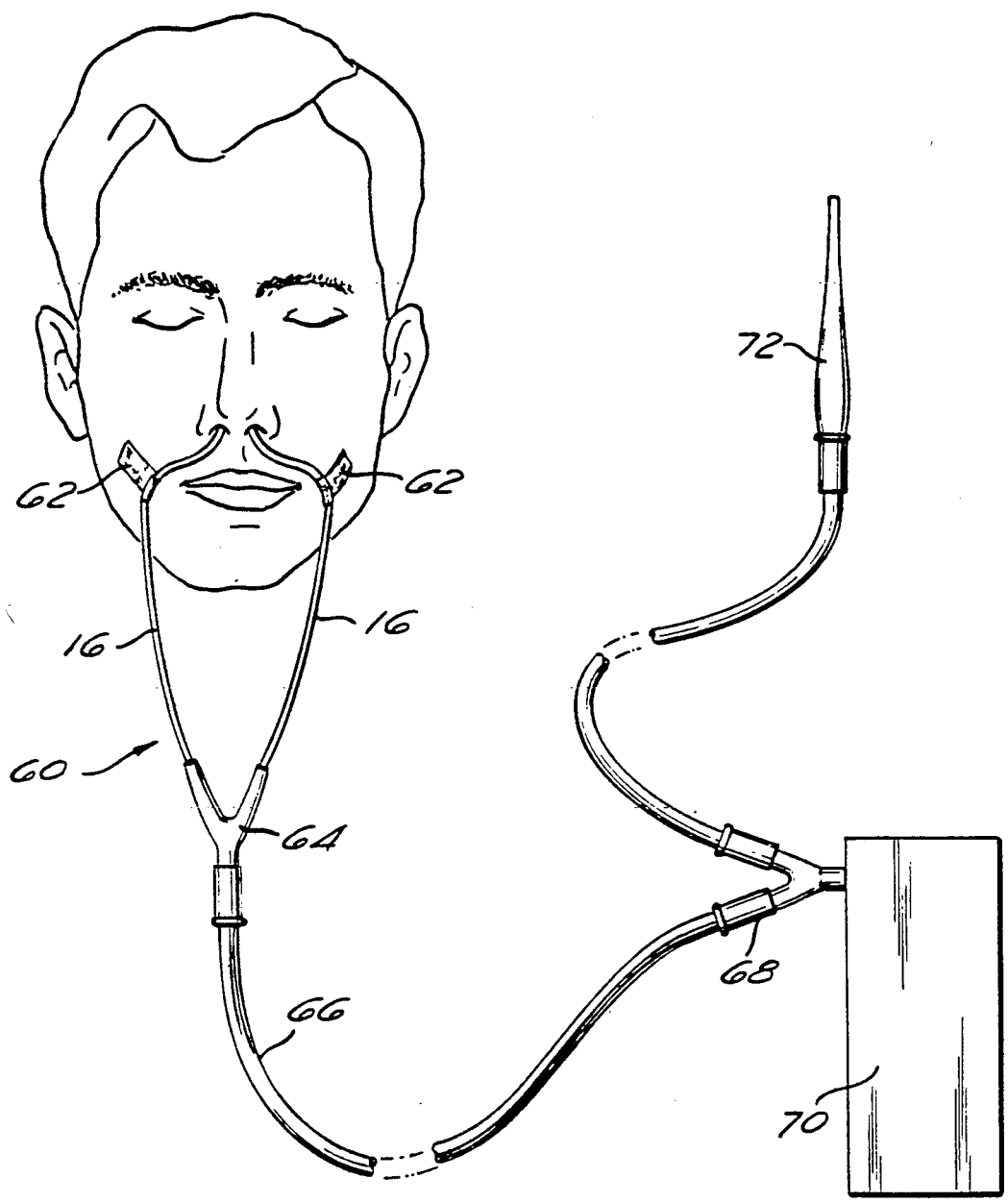
FIG. 11 illustrates a nasal device for concurrent placement in both nostrils, having a pair of drainage conduits joined together at a first Y-connector so as to channel the fluids being expelled from both nasal cavities into a single drainage conduit.

As illustrated in FIG. 11, the nasal tampon of the present invention may be modified in such a way that hemorrhaging in both nasal cavities, on opposite sides of the septum, may be controlled simultaneously. In this embodiment, the nasal tampon 60 is provided with two intranasal portions (not shown), each having a drainage conduit 16 which extends from the anterior nares and is conveniently secured on opposite sides of the face by adhesive tape 62. The tape 62 aids in stabilizing the tampon, 60 within the nasal cavity, and prevents the drainage conduits 16 from becoming entangled during the nasal procedure. The drainage conduits 6 are joined together at a Y-connector 64 which channels fluids being drainage conduit 66. Disposed at the distal end of the common drainage conduit 66 is a second Y-connector 68. The second Y-connector 68 is provided to allow two forms of suctioning devices to be used. If bleeding is profuse, it may be advantageous to utilize a suction machine 70 to continuously aspirate fluids from the nasal cavity If, however, bleeding has lessened to a degree where the suctioning power of an aspirating machine is not warranted, a hand held suctioning device 72 may be employed, to selectively void the nasal cavity of fluids.

MANNER OF USE OF THE NASAL TAMPON

The nasal tampon 10 of the present invention is adapted to control nasal hemorrhaging due to any number of causes. For a simple nasal hemorrhage which, for example, may be nothing more than a common nose bleed, the device 10 may be inserted through the anterior nares of the nasal cavity in its deflated state, as illustrated in FIG. 8. After the device has been inserted through the anterior nares, beyond the choanae, the expansible sealing cuff 18 is inflated. Preferably, the expansible sealing cuff 18 is inflated via a syringe (not shown), which is inserted into a simple one-way fluid valve 30, and forces air through the inflation conduit 14 and into the expansible cuff. After inflation, the syringe may be removed, without deflating the cuff 18, as the valve 30 prevents air from escaping the inflation conduit 14. Alternatively, a squeezable bulb (not shown) may be attached to the distal end of the inflation conduit in lieu of the fluid valve 30. In this case, the bulb is compressed to force air into the cuff 18, and remains attached to the inflation conduit 14 during a procedure. The nasal tampon 10 can then be pulled outwardly through the anterior nares, as indicated by the arrowhead 74 in FIG. 9, until the expansible sealing cuff 18 is seated within the nasopharyngeal passageway and forms a low pressure seal therewith (FIG. 10). Advantageously, when inserting the nasal tampon 10 in this manner, a slight resistance to the outward pulling will be sensed when the device is properly placed so that the low pressure cuff is seated within but not firmly wedged within the nasopharyngeal passageway and choanae.

A significant feature of this invention is that the low pressure cuff enables an effective seal to prevent blood, mucous and other fluids from seeping down the patient's throat without requiring that the cuff be firmly wedged within the nasopharyngeal passageway. A cuff or similar member wedged within the nasopharyngeal passageway will cause the patient extreme discomfort and adversely affect the patient's blood pressure.

Another significant feature of this invention is the provision of a bypass breathing lumen 50 which enables the patient to breathe through the nose. It has been shown that when the patient's natural breathing ability through the nose is enabled, the patient tends to show less signs of anxiety.

To assist in the proper placement of the device 10, a plurality of graduated markings 48 may be provided on one or both the inflation or drainage conduits 14, 16, respectively. The drainage conduit 16 may then be attached to a source of suction (not shown) so as to void the nasal cavity of all fluids accumulating in front of the expansible sealing cuff 18. Significantly, the absorptive member 42 is slidably mounted on the nasal tampon 10 and can either be suitably inserted into the nasal cavity before or subsequent to the inflation of the expansible sealing cuff 18. The blood and other liquid matter, collected in front of the sealing cuff 18, will be absorbed by the absorptive member 42, and removed therefrom through the influent ports 36 of the drainage conduit 16, and subsequently disposed of.

In general, the strength of the suction should be just that which is necessary to keep the area clear. Thus, the amount of nasal hemorrhaging will dictate the degree of suction required. If heavy bleeding is encountered, the degree of suction required may interfere with the patient's respiration through the breathing lumen. Depending on the amount of bleeding, the degree of suction should be varied so as not to interfere with the patient's breathing.

When the device 10 is to be used during a surgical nasal procedure, the patient is prepared in the standard way. To ensure the continued satisfactory operation of the device 10, it is desirable to line the device with a compound which will prevent adherence of blood or other liquid matter onto the device 10, and thereby maintain all of the passageways clear. Well suited for this purpose is a ZYLOCANE gel, which serves to lubricate the device as well as provide a local anesthetic to desensitize the area. The nasal tampon 10, in its deflated state, is of a sufficiently small diameter, which enables it to be inserted through the anterior nares of the nose, which may be spread apart using a conventional nasal speculum. No forceps are required, since the tampon 10 may be manipulated much like a catheter. Further, the inflation and drainage conduits 14, 16, respectively, are flexible so as to readily bend and follow the normal front to back curvature of the nasal cavity. The expansible low pressure sealing cuff 18 is readily collapsed around the inflation and drainage conduits 14, 16 to facilitate passage through the nares. Once suitably positioned within the nasal cavity, the expansible sealing cuff 18 may be inflated in the manner discussed above.

The device 10 is also suited for use in post operative situations, for example, following reconstructive surgery. Since the choanae is occluded by the expansible sealing cuff 18, the danger of the patient swallowing and/or choking on his own blood is substantially eliminated. This is significant in that when a patient has blood in his stomach, it tends to induce vomiting. The vomiting creates anxiety and straining which raises the patient's venous and arterial pressure, which in turn increases bleeding. The increase in bleeding increases nausea, and the whole cycle escalates.

Thus, it has been shown that the improved nasal tampon 10 of the present invention has several significant advantages over prior art devices. A significant advantage of the present invention resides in the novel design and nature of the expansible sealing cuff 18. The cuff 18 is advantageously constructed such that, when inflated, an extended cylindrical low pressure sealing surface is presented, which conforms to the shape of the bony structure of the choanae. This low pressure seal is just sufficient to occlude the choanae and prevent the flow of blood and other fluids down the throat of the patient while the device is operatively installed. It has been found that a low intracuff pressure of under only 25 mmHg is sufficient to form an adequate seal. In contrast, prior art nasal tampons employing inflatable cuffs typically require substantially higher pressures.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. A method of controlling nasal hemorrhaging during a nasal operation or other nasal procedure without exerting direct pressure on the area of bleeding, comprising the steps of:
   inserting a low pressure expandable sealing cuff into the nasal cavity of a patient through the anterior nares;
   inflating said cuff to a sufficiently low intracuff pressure that will cause said cuff to occlude the choanae without causing damage to the mucosal tissue due to pressure necrosis;
   absorbing the blood, mucous and other debris, collected in front of said expandable cuff within the nasal cavity; and
   suctioning the blood, mucous and other debris, collected in front of said expansible cuff out of the nasal cavity.

2. A method of controlling nasal hemorrhaging during a nasal operation or other nasal procedure without exerting direct pressure on the area of bleeding, comprising the steps of:
   inserting a nasal tampon, having a low pressure expansible sealing cuff into the nasal cavity of a patient through the anterior nares;
   inflating said cuff to a sufficiently low intracuff pressure that will cause said cuff to occlude the choanae without causing damage to the mucosal tissue due to pressure necrosis; and
   sliding an absorptive member over said nasal tampon and into said nasal cavity so as to absorb said blood.

3. A method of controlling nasal hemorrhaging during a nasal operation or other nasal procedure without exerting direct pressure on the area of bleeding, as defined by claim 2, further comprising the step of:
   suctioning the blood, mucous and other debris, collected in front of said expansible cuff and in said absorptive member out of the nasal cavity.

4. A method of controlling nasal hemorrhaging during a nasal procedure or other nasal procedure without exerting direct pressure on the area of bleeding, as defined by claim 2, wherein said expansible sealing cuff is inflated to an intracuff pressure which does not exceed 25 mmHg.

5. A method of controlling nasal hemorrhaging, comprising the steps of:
   providing a nasal tampon having a low pressure expandable sealing cuff disposed near one end;
   inserting said nasal tampon into a nasal cavity so that said cuff is beyond the choanae;
   inflating said expandable sealing cuff;
   withdrawing said nasal tampon until said cuff is seated into the posterior choanae, forming a low pressure seal therebetween; and
   providing an absorptive member for absorbing fluids accumulating in front of said sealing cuff.

6. A method, as defined by claim 5, further comprising the step of suctioning fluids from said nasal cavity and said absorptive member accumulating in front of said sealing cuff.

* * * * *